(12) United States Patent
Krammer et al.

(10) Patent No.: US 9,629,795 B2
(45) Date of Patent: Apr. 25, 2017

(54) SUBSTANCE MIXTURES

(71) Applicant: Symrise AG, Holzminden (DE)

(72) Inventors: Gerhard Krammer, Holzminden (DE); Sven Siegel, Höxter (DE); Deborah Kennison, Wayne, NJ (US)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 14/672,843

(22) Filed: Mar. 30, 2015

(65) Prior Publication Data

US 2015/0272864 A1    Oct. 1, 2015

Related U.S. Application Data

(60) Provisional application No. 61/973,365, filed on Apr. 1, 2014.

(51) Int. Cl.

| | | |
|---|---|---|
| *A61K 8/97* | (2017.01) | |
| *A61K 8/31* | (2006.01) | |
| *A61Q 11/00* | (2006.01) | |
| *A23G 3/36* | (2006.01) | |
| *A23L 3/3463* | (2006.01) | |
| *A23L 1/235* | (2006.01) | |
| *A61K 8/34* | (2006.01) | |
| *A23L 2/52* | (2006.01) | |
| *A23L 2/60* | (2006.01) | |
| *A23G 3/48* | (2006.01) | |
| *A23G 4/06* | (2006.01) | |
| *A23L 27/00* | (2016.01) | |
| *A23L 27/12* | (2016.01) | |
| *A23L 27/29* | (2016.01) | |
| *A23L 27/30* | (2016.01) | |

(52) U.S. Cl.
CPC ............... *A61K 8/97* (2013.01); *A23G 3/36* (2013.01); *A23G 3/48* (2013.01); *A23G 4/06* (2013.01); *A23G 4/068* (2013.01); *A23L 2/52* (2013.01); *A23L 2/60* (2013.01); *A23L 27/13* (2016.08); *A23L 27/29* (2016.08); *A23L 27/36* (2016.08); *A23L 27/70* (2016.08); *A23L 27/72* (2016.08); *A61K 8/31* (2013.01); *A61K 8/345* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 2009/0196972 A1* | 8/2009 | Monsalve-Gonzalez | A23L 1/221 426/534 |
| 2009/0318321 A1 | 12/2009 | Hood et al. | |
| 2012/0003163 A1 | 1/2012 | Mordas et al. | |
| 2012/0322892 A1 | 12/2012 | Xie et al. | |
| 2013/0040036 A1 | 2/2013 | Zeller et al. | |
| 2013/0189399 A1 | 7/2013 | Ragnarsson et al. | |
| 2013/0236597 A1* | 9/2013 | Dierbach | A23L 1/22083 426/3 |
| 2013/0236620 A1 | 9/2013 | Herrera-Gomez et al. | |
| 2013/0295259 A1* | 11/2013 | Dierbach | A23L 1/22083 426/533 |
| 2013/0303423 A1 | 11/2013 | Fenyvesi et al. | |

FOREIGN PATENT DOCUMENTS

CN    101 921 543 A    12/2010

OTHER PUBLICATIONS

Pamela L. Crowell. Prevention and Therapy of Cancer by Dietary Monoterpenes. J. Nutr. 129: 775S-778S, 1999.*
Nakata et al, "Volatile Components of Essential Oil from Cultivated Myrica gale var. tomentosa and Its Antioxidant and Antimicrobial Activities," J Oleo Sci., vol. 62, No. 9, Jan. 1, 2013, pp. 755-762.
Buettner et al, "Evaluation of Aroma Differences between Hand-Squeezed Juices from Valencia Late and Navel Oranges by Quantitation of Key Odorants and Flavor Reconstitution Experiments," J. Agric. Food Chem 2001, vol. 49. No. 5, May 1, 2001, pp. 2387-2394.

* cited by examiner

*Primary Examiner* — Frederick Krass
*Assistant Examiner* — Michael P Cohen
(74) *Attorney, Agent, or Firm* — Dilworth & Barrese, LLP

(57) ABSTRACT

Substance mixtures are proposed, comprising
(a) terpenes,
(b) propane-1,3-diol, and optionally
(c) active substances selected from the group consisting of
(c1) rebaudiosides or plant extracts comprising them,
(c2) steviosides or plant extracts comprising them,
(c3) monatin,
(c4) naringin,
(c5) chalcones and hydrochalcones,
(c6) mogrosides or plant extracts comprising them,
(c7) rubusosides or plant extracts comprising them, and
(c8) glycyrrhizic acid or plant extracts comprising it.

5 Claims, No Drawings

SUBSTANCE MIXTURES

FIELD OF THE INVENTION

The invention is located in the field of the aroma substances and relates to novel substance mixtures comprising terpenes and specific complementary substances, to foodstuffs comprising them, to a method of enhancing stability, and to the use of the complementary substances as stabilizers.

PRIOR ART

From the botanical point of view, citrus plants are a plant genus from the rue family (Rutaceae), which have their natural habitat in the tropical and subtropical regions of South-East Asia. For the chemist, in particular the food chemist, citrus fruits are unique sources of a large number of monocyclic terpenes, which share the fact that they have the unique citrus odor and flavor, which is normally considered to be a synonym for freshness and cleanness. The fact that approximately 20% of all Internet entries on this subject are related to cookery proves that citrus aromas are also important for gourmets.

On the whole, citrus aromas in general and monocyclic terpenes in particular are important commercial products for the aroma substance industry. A considerable disadvantage is that the substances are generally highly sensitive to oxidization. For example, d-limonene is known to be degraded in the air to give carvone, carveol and terpineol. In this process, the fruity, citrus and orange notes are masked by the intensely spicy and herbaceous taste notes of the degradation products. It is particularly the caraway note of d-carvone which very rapidly comes to the fore, which is extraordinarily undesirable from the point of view of the food technician who wishes to create a product with citrus flavor.

The problem of the terpenes' lack of oxidation resistance is known from the literature, and there has therefore been no lack of attempts to prevent, or at least slow down, the substances' oxidative degradation. Approaches in which known antioxidants, such as, for example, BHT, BHA or tocopherol, have been added have proved to be unsatisfactory, in particular because the presence of these additions is also not desirable in foodstuffs [cf. Kimura et al., J. Agricult. Food Chem. 31, 800-804 (1983), ibid. 47, 1661-1663 (1983).]. The international patent application WO 1998 058656 A1 (Hauser) proposes to stabilize the citrus components by adding rosmarinic acid, but this alternative, too, proves to be insufficient under practice conditions.

Instead of stabilizing the citrus components by additives, the alternative of excluding the oxygen by encapsulating the terpenes is found in the literature. Thus, for example, U.S. Pat. No. 5,603,952 (Soper) proposes to enclose terpenes in capsules made of fish gelatin. However, this greatly limits the field of application of the products, because capsules are not desired in all applications.

Subject-matter of US 2007 0116819 A1 is sweetener compositions which essentially comprise the natural "high-potential sweeteners" together with omega-unsaturated fatty acids and optionally additives which influence the taste of the mixtures. Example A1 discloses a diet drink which comprises rebaudioside A as sweetener. Erythritol is added to enhance the sweetening action. The mixture also comprises limonene, which, however, only acts as a dispersant.

WO 2005 048743 A1 discloses foodstuffs which have a fruit component and which combine various freshness components (for example menthol) with coolants. Sweeteners, such as, for example, stevia, may also be present. The examiner cites this document as novelty-injurious for claims 1, 4 and 13. Table 6 discloses a preparation comprising menthol and stevia, the quantitative ratio being 0.25:99.75.

Subject-matter of EP 2298084A1 is sweetener-reduced products which combine natural sweeteners with phyllodulcin. Paragraph 144 discloses a preparation which combines rebaudioside with various coolants which have a cyclic monoterpene structure. The weight ratio of rebaudioside to monoterpene in formulation A is 13:87 and in formulation B is 5:9.

It is known, furthermore, from the two international patent applications WO 2013 134532 A1 and WO 2013 134607 A1 (KRAFT FOODS) that the aroma of foodstuffs in general, and of wholegrain products and drinks in particular, can be altered by addition of 1,3-propanediol. The specifications, however, include no reference to the specific problems affecting the stabilization of monocyclic terpenes.

The object of the present invention was therefore that of inhibiting or at least strongly suppressing the oxidative degradation of monocyclic compounds, and in that way maintaining, or even further enhancing, the citrus taste in foodstuff preparations over the storage time, at the same sensory level.

DESCRIPTION OF THE INVENTION

Subject-matter of the invention is substance mixtures comprising
(a) terpenes,
(b) propane-1,3-diol, and optionally
(c) active substances selected from the group consisting of
(c1) rebaudiosides or plant extracts comprising them,
(c2) steviosides or plant extracts comprising them,
(c3) monatin,
(c4) naringin,
(c5) chalcones and hydrochalcones,
(c6) mogrosides or plant extracts comprising them,
(c7) rubusosides or plant extracts comprising them, and
(c8) glycyrrhizic acid or plant extracts comprising it.

Surprisingly it has been found that through the addition of propane-1,3-diol, the oxidative degradation of the terpenes, especially of monoterpenes or sesquiterpenes, is greatly reduced. The residual amounts of unwanted degradation products are then also masked by the presence of the diol. The outcome of this is that the addition of propane-1,3-diol to limonene leads in fact to an intensification of the citrus taste. These effects can be further enhanced by the addition to the substance mixtures of active substances of group c, especially rebaudioside A.

Terpenes

Most terpenes especially monoterpenes and sesquiterpenes (component a), are derived from p-menthane and have a cyclohexane skeleton. Besides menthane, the most important representatives include phellandrene, terpinolene, terpinene, cymene and limonene.

For the purposes of the invention, limonene is the preferred terpene since it is highly important in terms of application and is particularly susceptible to oxidative degradation. The substance occurs as two enantiomers, namely (R)-(+)-limonene (also referred to as D-(+) or (+)-limonene for short) and (S)-(−)-limonene (also referred to as L-(−)-limonene or (−)-limonene). The racemate of the two enantiomers is also called dipentene.

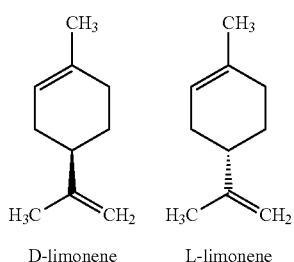

D-limonene    L-limonene

For the purposes of the present invention, D-limonene is the preferred monocyclic terpene.

Active Substances

The active substances which form group (c) are elucidated in more detail below.

Rebaudiosides belong to the steviosides, the main components of the plant *Stevia rebaudiana*, also referred to as sweetleaf or sugarleaf.

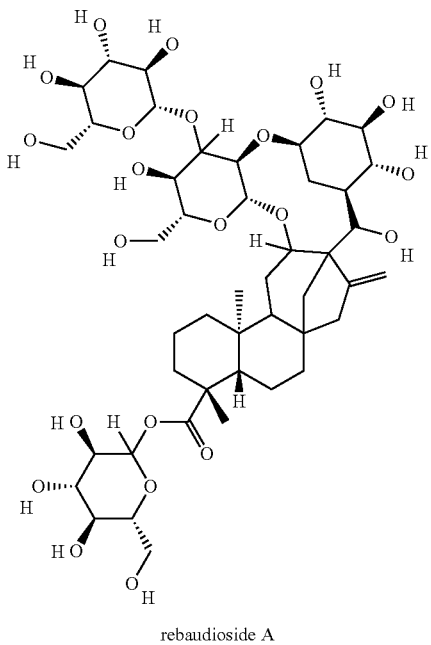

rebaudioside A

10% of the leaves' dry matter is accounted for by the diterpene glycoside stevioside, followed by rebaudioside A (2 to 4% by weight) and ten further steviol glycosides, such as, for example, dulcoside. Rebaudiosides and stevia extract are nowadays approved in most countries as sweeteners; a daily intake of up to 4 mg stevioside per kilogram bodyweight is considered to be acceptable. For the purposes of the invention, it is possible to employ individual rebaudiosides or the extracts of the stevia plant. Particularly preferred, however, is the use of rebaudioside A, since this substance features lower bitterness and the highest sweetening power. The substance mixtures according to the invention may comprise components (a) and (b) in a weight ratio of from approximately 1:99 to approximately 99:1, preferably approximately 25:75 to approximately 75:25 and particularly approximately 40:60 to approximately 60:40.

Various other active substances which likewise enhance the citrus note without featuring any fruit aroma themselves may also be employed as an alternative or in addition to the rebaudiosides and/or stevia extracts as component (c); they are:

monatin, naringin, chalcones and hydrochalcones, especially dihydrochalcones, mogrosides and extracts of plants of the genus *Rubus*.

Monatin, also known as arruva, is a natural sweetener which can be isolated from the plant *Sclerochiton ilicifolius*.

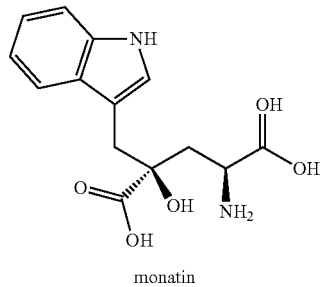 [SMILES: N[C@@H](C[C@@](O)(Cc1c[nH]c2ccccc12)C(=O)O)C(=O)O]

monatin

Naringin is a polyphenolic glycoside which is found in grapefruit and pomelo and which imparts a bitter taste to these fruits. The substance is known in particular for its hypolipidemic activity.

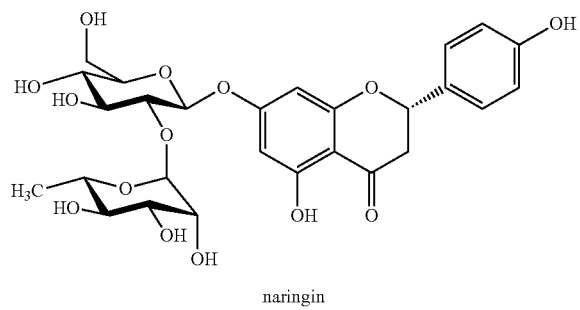

naringin

The chalcones and hydrochalcones, too, are polyphenols; the representatives naringin dihydrochalcone and neohesperidin dihydrochalcone, and phloretin, which are known as artificial sweeteners, must be emphasized in particular:

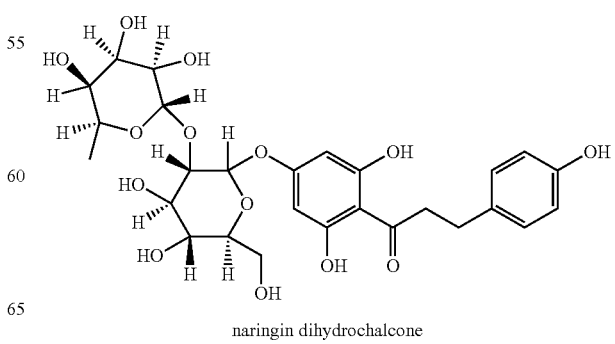

naringin dihydrochalcone

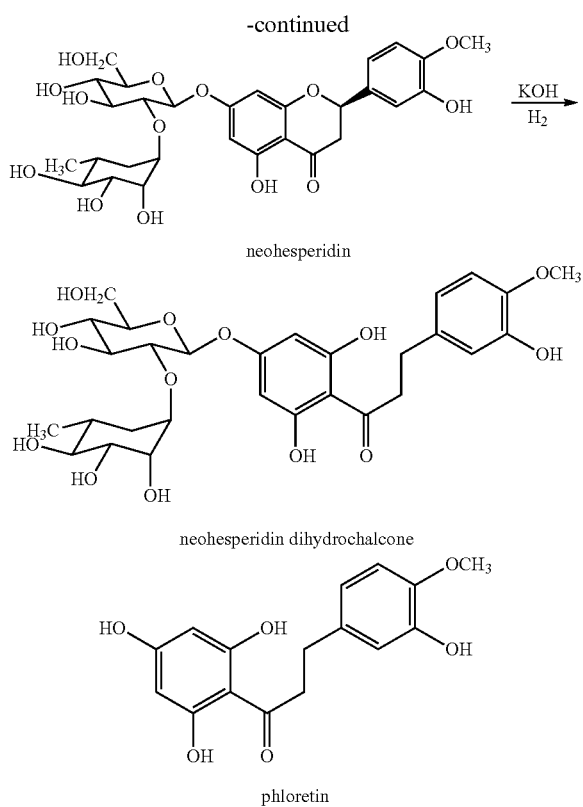

neohesperidin neohesperidin dihydrochalcone phloretin

The term mogrosides refers to a group of cucurbitan glycosides which are known as a component of the natural sweetener luo han guo (from *Momordica grosvenorii*, for example). Mogroside-5, which is 400 times sweeter than sugar, must be emphasized here.

*Rubus arcticu, Rubus strigosus, Rubus armeniacus, Rubus caesius, Rubus chamaemorus, Rubus corylifolius* agg., *Rubus fruticosus* agg., *Rubus geoides, Rubus glaucus, Rubus gunnianus, Rubus idaeus, Rubus illecebrosus, Rubus laciniatus, Rubus leucodermis, Rubus loganobaccus, Rubus loxensis, Rubus nepalensis, Rubus nessensis, Rubus nivalis, Rubus odoratus, Rubus pentalobus, Rubus phoenicolasius, Rubus saxatilis, Rubus setchuenensis, Rubus spectabilis* and *Rubus ulmifolius* and their mixtures. These are essentially extracts of different blackberry and raspberry species with a ruboside content. Extracts of *Rubus suavissimus* are preferred.

Surprisingly it has been found that the addition of glycyrrhizic acid or a corresponding salt or an extract comprising this substance further boosts the citrus note in the substance mixtures.

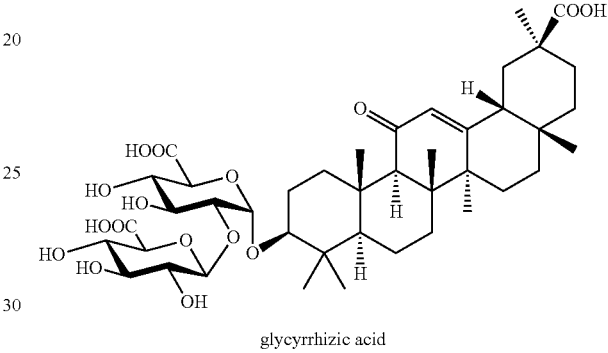

glycyrrhizic acid

Again, this finding per se could not have been predicted, because glycyrrhizic acid and the glycyrrhinates have an intense liquorice flavor. It is possible for the purposes of the invention to employ the acid itself, its salts—for example

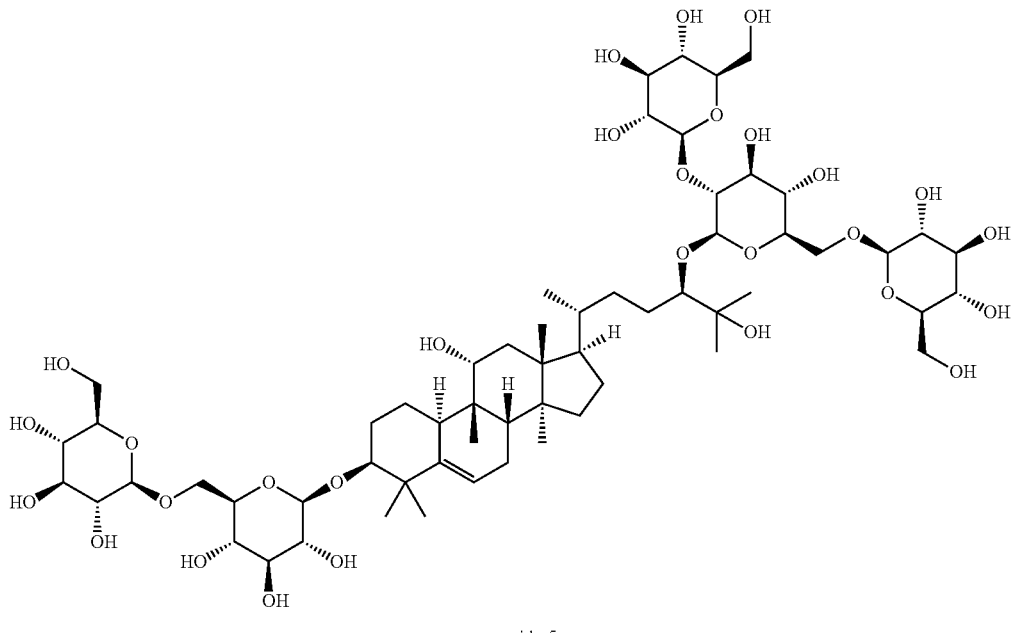

mogroside-5

Finally suitable as component (c) are extracts of plants selected from the group consisting of *Rubus allegheniensis,* sodium, potassium or ammonium salt—or the extracts of the plant *Glycyrrhiza glabra*. Especially preferred is monoammonium glycyrrhizate.

Where individual compounds have been specified above as component (c), such specification also encompasses extracts of plants which comprise significant amounts of these substances.

Extraction Methods

If the above has referred to extracts, the latter may be prepared in a manner known per se, i.e. for example by means of an aqueous, alcoholic or aqueous-alcoholic extraction of the plants or plant parts or of the leaves or fruits. All traditional extraction methods, such as, for example, maceration, remaceration, digestion, agitation maceration, fluidized-bed extraction, ultrasound extraction, countercurrent extraction, percolation, repercolation, evacolation (extraction under reduced pressure), diacolation or solid-liquid extraction under continuous reflux are suitable. A method which is advantageous for use on an industrial scale is the percolation method. Fresh plants or plant parts may be employed as starting material; usually, however, the starting material will be dry plants and/or plant parts which may be comminuted mechanically before the extraction. Suitable for this purpose are all comminutation methods known to a person skilled in the art; an example which may be mentioned is freeze-grinding. Solvents which can be used for carrying out the extractions may be organic solvents, water (preferably hot water with a temperature of above 80° C. and in particular above 95° C.) or mixtures of organic solvents and water, in particular low-molecular-weight alcohols with higher or less high water contents.

Particular preference is given to the extraction with methanol, ethanol, pentane, hexane, heptane, acetone, propylene glycols, polyethylene glycols and ethyl acetate and mixtures of these, and their aqueous mixtures. The extraction is usually carried out at 20 to 100° C., preferably at 30 to 90° C., in particular at 60 to 80° C. In a preferred embodiment, the extraction is carried out under an inert gas atmosphere so as to avoid oxidation of the active substances of the extract. This is important in particular in the case of extractions at temperatures of above 40° C. The extraction times are adjusted by the person skilled in the art as a function of the starting material, the extraction method, the extraction temperature, the ratio of solvent to raw material, etc.

After the extraction, the resulting crude extracts may optionally be subjected to further customary steps such as, for example, purification, concentration and/or decoloration. If desired, the extracts thus prepared may be subjected, for example, to a selective removal of individual undesired ingredients. The extraction can be carried out to any desired degree of extraction, but is usually carried out exhaustively. Typical yields (=dry matter weight of the extract relative to amount of raw material employed) in the extraction of dried leaves are in the range of from 3 to 15, in particular 6 to 10% by weight. The present invention comprises the knowledge that the extraction conditions and the yields of the final extracts can be selected by one skilled in the art depending on the desired field of application. These extracts which, as a rule, have active substance contents (=solids contents) in the range of from 0.5 to 10% by weight can be employed as such; however, it is also possible to fully remove the solvent by drying, in particular by spray-drying or freeze-drying, in which case a deep red solid remains.

The extracts may also be used as starting materials for obtaining the abovementioned pure active substances, unless the latter can be prepared more simply and with less financial outlay by the synthetic route. Accordingly, the active substance content of the extracts may amount to from 5 to 100, preferably from 50 to 95% by weight. The extracts themselves may be present as aqueous preparations and/or as preparations which are dissolved in organic solvents, and also as spray-dried or freeze-dried anhydrous solids. Organic solvents which are suitable in this context are, for example, the aliphatic alcohols having 1 to 6 carbon atoms (for example ethanol), ketones (for example acetone), halohydrocarbons (for example chloroform or methylene chloride), lower esters or polyols (for example glycerol or glycols).

Substance Mixtures

In a first preferred embodiment, the substance mixtures may comprise components (a), (b) and (c) in a weight ratio of approximately 1:(0.1 to 20):(0 to 20) and more particularly in a weight ratio of approximately 1:(0.1 to 10):(0.1 to 10).

A second preferred embodiment is directed to substance mixtures comprising
(a) 20 to 80% by weight of limonene and
(b) 80 to 20% by weight of propane-1,3-diol
with the proviso that the quantity figures add up to 100% by weight.

A third preferred embodiment encompasses substance mixtures comprising
(a) 10 to 50% by weight of limonene,
(b) 45 to 25% by weight of propane-1,3-diol and
(c) 45 to 25% by weight of active substances
with the proviso that the quantity figures add up to 100% by weight.

Furthermore, the substance mixtures can be distinguished by the fact that they have a water content of less than approximately 2 and in particular of less than approximately 1% by weight. By preference, the mixtures are entirely anhydrous. To this end, aqueous and/or alcoholic solutions or dispersions of the substance mixtures may be dried, for example by spray-drying, fluidized-bed drying or lyophilization (freeze-drying). The dry preparations may subsequently be either ground or granulated.

Encapsulation

The preparations are customarily encapsulated using solid coating materials, such as starches, for example, including their degradation products and also chemically or physically produced derivatives (especially dextrins and maltodextrins), gelatin, gum arabic, agar-agar, ghatti gum, gellan gum, modified and nonmodified celluloses, pullulan, curdlan, carrageenans, alginic acid, alginates, pectin, inulin, xanthan gum, and mixtures of two or more of these substances.

The solid encapsulation material is preferably a gelatin (more particularly pork, beef, poultry and/or fish gelatin), preferably with a swelling factor of greater than or equal to 20, preferably of greater than or equal to 24. Likewise preferred are maltodextrins (especially those based on cereals, specifically corn, wheat, tapioca, or potatoes), preferably with DE values in the range from 10 to 20. Further preferred are celluloses (e.g. cellulose ethers), alginates (e.g. sodium alginate), carrageenan (e.g. beta-, iota-, lambda- and/or kappa-carrageenan), gum arabic, curdlan and/or agar-agar.

Particularly preferred among these substances is gelatin, since it is readily available and can be acquired with different swelling factors. Especially preferred, particularly for oral applications, are seamless gelatin or alginate capsules, with an envelope which breaks up or dissolves very rapidly in the mouth or when chewed. Such capsules are described comprehensively for example in the following specifications: EP 0389700 A1, U.S. Pat. No. 4,251,195, U.S. Pat. No. 6,214,376, WO 2003 055587 or WO 2004 050069 A1.

The capsules may alternatively also represent microcapsules. The terms "microcapsules" or "nanocapsules" are taken by the skilled worker to mean spherical aggregates with a diameter in the range of from approximately 0.0001 to approximately 5 and preferably 0.005 to 0.5 mm and which comprise at least one solid or liquid core which is enclosed by at least one continuous envelope. More precisely, they are finely-dispersed liquid or solid phases which are enveloped by film-forming polymers and during whose preparation the polymers, after emulsification and coacervation or interface polymerization, precipitate on the material to be enveloped. In a different method, molten waxes are taken up in a matrix ("microsponge") which, as microparticles, may additionally be enveloped by film-forming polymers. In a third method, particles are coated in turn with differently charged polyelectrolytes ("layer-by-layer" method). The microscopic capsules may be dried like powders. Besides single-core microcapsules, multi-core aggregates, which comprise two or more cores distributed within continuous enveloping material, also referred to as microspheres, are also known. Single- or multi-core microcapsules may additionally be enclosed by another second, third etc. envelope. The envelope may be composed of natural, semisynthetic or synthetic materials. Examples of natural enveloping materials are gum arabic, agar-agar, agarose, maltodextrins, alginic acid or its salts, for example sodium alginate or calcium alginate, fats and fatty acids, cetyl alcohol, collagen, chitosan, lecithins, gelatin, albumin, shellac, polysaccharides such as starch or dextran, polypeptides, protein hydrolysates, sucrose and waxes. Semisynthetic enveloping materials are, inter alia, chemically modified celluloses, in particular cellulose esters and cellulose ethers, for example cellulose acetate, ethylcellulose, hydroxypropylcellulose, hydroxypropylmethylcellulose and carboxymethylcellulose, and starch derivatives, in particular starch ethers and starch esters. Examples of synthetic enveloping materials are polymers such as polyacrylates, polyamides, polyvinyl alcohol or polyvinylpyrrolidone.

Examples of prior-art microcapsules are the following commercial products (the enveloping material is in each case given in parentheses): Hallcrest Microcapsules (gelatin, gum arabic), Coletica Thalaspheres (maritime collagen), Lipotec Millicapseln (alginic acid, agar-agar), Induchem Unispheres (lactose, microcrystalline cellulose, hydroxypropylmethylcellulose); Unicerin C30 (lactose, microcrystalline cellulose, hydroxypropylmethylcellulose), Kobo Glycospheres (modified starch, fatty acid esters, phospholipids), Softspheres (modified agar-agar) and Kuhs Probiol Nanospheres (phospholipids), and also Primaspheres and Primasponges (chitosan, alginates) and Primasys (phospholipids).

Chitosan microcapsules and processes for producing them are well-known from the prior art [WO 01/01926, WO 01/01927, WO 01/01928, WO 01/01929]. Microcapsules having average diameters in the range from 0.0001 to 5, preferably 0.001 to 0.5 and more particularly 0.005 to 0.1 mm, consisting of an envelope membrane and a matrix comprising the active substances, may be obtained, for example, by (a) preparing a matrix from gel formers, cationic polymers and active substances,
(b) optionally dispersing the matrix in an oil phase,
(c) treating the dispersed matrix with aqueous solutions of anionic polymers, and optionally removing the oil phase.

Steps (a) and (c) here are interchangeable if anionic polymers are used in step (a) in place of the cationic polymers, and vice versa.

The capsules can also be produced by enveloping the active substance in alternation with layers of differently charged polyelectrolytes (layer-by-layer technology). In this context, reference may be made to European patent EP 1064088 B1 (Max-Planck Gesellschaft).

Preparations for Oral Consumption

A further subject of the invention encompasses preparations for oral consumption which comprise the substance mixtures according to the invention preferably in amounts of approximately 0.01 to approximately 1% by weight, in particular approximately 0.05 to approximately 0.5% by weight and particularly preferably from approximately 0.8 to approximately 0.1% by weight. These preparations may on the one hand be foods, especially bakery products, drinks, chewing gums, confectionery products and the like, or else oral and dental care compositions.

Foodstuffs

The oral preparations preferably comprise bakery products, for example bread, dry biscuits, cakes, other baked goods, confectionery products (for example chocolates, chocolate bar products, other bar products, fruit gums, hard and soft caramels, chewing gum), alcoholic or non-alcoholic drinks (for example coffee, tea, iced tea, wine, wine-containing drinks, beer, beer-containing drinks, liqueurs, schnapps, brandies, (carbonated) fruit-containing lemonades, (carbonated) isotonic drinks, (carbonated) soft drinks, nectars, spritzers, fruit and vegetable juices, fruit or vegetable juice preparations, instant drinks (for example instant cocoa drinks, instant tea drinks, instant coffee drinks, instant fruit drinks), meat products (for example hams, fresh sausage or uncooked sausage preparations, seasoned or marinated fresh or pickled meat products), eggs or egg products (dried egg, egg white, egg yolk), cereal products (for example breakfast cereals, muesli bars, prefermented ready-to-serve rice products), milk products (for example milk drinks, buttermilk drinks, dairy ice cream, yoghurt, kefir, fresh cheese, soft cheese, hard cheese, dried milk powder, whey, whey drinks, butter, buttermilk, products containing partially or fully hydrolyzed milk protein), products of soya protein or other soya bean fractions (for example soya milk and products made therefrom, fruit drinks containing soya protein, soy lecithin-containing preparations, fermented products such as tofu or tempeh or products made therefrom), products of other plant protein sources, for example oat protein drinks, fruit preparations (for example jams, fruit ice cream, fruit sauces, fruit fillings), vegetable preparations (for example ketchup, sauces, dried vegetables, frozen vegetables, precooked vegetables, bottled vegetables), snack articles (for example baked or fried potato chips or potato dough products, corn or peanut-based extrudates), fat- and oil-based products or emulsions of the same (for example mayonnaise, remoulade, dressings), other ready-to-serve meals and soups (for example dried soups, instant soups, precooked soups), spices, spice mixtures and also in particular seasonings which are used, for example, in the snack sector.

Food Ingredients

The foodstuffs may contain further ingredients, such as, for example, sweeteners, food acids, acidity regulators, thickeners, and in particular aroma substances.

Sweeteners

As sweeteners, or sweet-tasting additives, firstly carbohydrates and especially sugars come into consideration, such as, for instance sucrose/saccharose, trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, or maltodextrin. Equally suitable are plant preparations which contain these substances, for example based on sugar beets (*Beta vulgaris* ssp., sugar fractions, sugar syrup, molasses), sugarcane (*Saccharum officinarum* ssp., molasses, sugarcane syrup), maple syrup (*Acer* ssp.) or agave (agave thick juice).

Those which also come into consideration are
- synthetic, i.e. generally enzymatically produced starch or sugar hydrolysates (invert sugar, fructose syrup);
- fruit concentrates (e.g. based on apples or pears);
- sugar alcohols (e.g. erythritol, threitol, arabitol, ribotol, xylitol, sorbitol, mannitol, dulcitol, lactitol);
- proteins (e.g. miraculin, monellin, thaumatin, curculin, brazzein);
- sweeteners (e.g. MAGAP, sodium cyclamate, acesulfame K, neohesperidin dihydrochalcone, saccharin sodium salt, aspartame, superaspartame, neotame, alitame, sucralose, steviosides, rebaudiosides, lugduname, carrelame, sucrononates, sucrooctates, monatin, phenylodulcin);
- sweet-tasting amino acids (e.g. glycine, D-leucine, D-threonine, D-asparagine, D-phenylalanine, D-tryptophan, L-proline);
- further sweet-tasting low-molecular-weight substances such as, e.g., hernandulcin, dihydrochalcone glycosides, glycyrrhizin, glycyrrhetic acid, derivatives and salts thereof, extracts of liquorice (*Glycyrrhizza glabra* ssp.), *Lippia dulcis* extracts, *Momordica* ssp. extracts or individual substances such as, e.g., *Momordica grosvenori* [luo han guo] and the mogrosides obtained therefrom, *Hydrangea dulcis* or extracts of *Stevia* ssp (e.g. *Stevia rebaudiana*).

Food Acids

The foods can contain carboxylic acids. Acids in the context of the invention are preferably acids permitted in foods, in particular those mentioned here:
E 260—acetic acid
E 270—lactic acid
E 290—carbon dioxide
E 296—malic acid
E 297—fumaric acid
E 330—citric acid
E 331—sodium citrate
E 332—potassium citrate
E 333—calcium citrate
E 334—tartaric acid
E 335—sodium tartrate
E 336—potassium tartrate
E 337—sodium-potassium tartrate
E 338—phosphoric acid
E 353—metatartaric acid
E 354—calcium tartrate
E 355—adipic acid
E 363—succinic acid
E 380—triammonium citrate
E 513—sulfuric acid
E 574—gluconic acid
E 575—glucono-delta-lactone Acidity Regulators Acidity regulators are food additives which keep constant the acidity or basicity and thereby the desired pH of a food. They are mostly organic acids and salts thereof, carbonates, and more rarely also inorganic acids and salts thereof. The addition of an acidity regulator partly increases the stability and firmness of the food, effects a desired precipitation and improves the action of preservatives. In contrast to acidulants, they are not used for taste modification of foods. Their action is based on the formation of a buffer system in the food in which the pH is not changed or is changed only slightly on addition of acidic or basic substances. Examples are:
E 170—calcium carbonate
E 260-263—acetic acid and acetates
E 270—lactic acid
E 296—malic acid
E 297—fumaric acid
E 325-327—lactates (lactic acid)
E 330-333—citric acid and citrates
E 334-337—tartaric acid and tartrates
E 339-341—orthophosphates
E 350-352—malates (malic acid)
E 450-452—di-, tri- and polyphosphates
E 500-504—carbonates (carbon dioxide)
E 507—hydrochloric acid and chlorides
E 513-517—sulfuric acid and sulfates
E 524-528—hydroxides
E 529-530—oxides
E 355-357—adipic acid and adipates
E 574-578—gluconic acid and gluconates Thickeners Thickeners are substances which are primarily able to bind water. By withdrawal of unbound water, the viscosity increases. From a concentration which is characteristic for each thickener, in addition to this effect, network effects also occur which lead to a usually disproportional increase in viscosity. In this case molecules are said to "communicate" with one another, i.e. become entangled. Most thickeners are linear or branched macromolecules (e.g. polysaccharides or proteins) which can interact with one another via intermolecular interactions, such as hydrogen bonds, hydrophobic interactions or ionic relationships. Extreme cases of thickeners are sheet silicates (bentonites, hectorites) or hydrated $SiO_2$ particles which are present in dispersed form as particles and can bind water in their solid-like structure or, on account of the described interactions, can interact with one another. Examples are:
E 400—alginic acid
E 401—sodium alginate
E 402—potassium alginate
E 403—ammonium alginate
E 404—calcium alginate
E 405—propylene glycol alginate
E 406—agar agar
E 407—carrageenan, furcelleran
E 407—carob bean meal
E 412—guar kernel meal
E 413—tragacanth
E 414—gum arabic
E 415—xanthan
E 416—karaya (Indian tragacanth)
E 417—tara gum meal (Peruvian carob bean meal)
E 418—gellan
E 440—pectin, Opekta
E 440ii—amidated pectin
E 460—microcrystalline cellulose, cellulose powder
E 461—methylcellulose
E 462—ethylcellulose
E 463—hydroxypropylcellulose E 465—methylethylcellulose E 466—carboxymethylcellulose, sodium carboxymethylcellulose Aroma Substances The invention in particular also permits the use of aroma substances with ester, aldehyde or lactone structure, which are degraded particularly rapidly in the presence of titanium dioxide and under the influence of light. The invention therefore also provides for enhanced stability, especially storage stability, of the aroma substances.

The oral preparations according to the invention can contain one or more aroma substances. Typical examples include: acetophenone, allyl caproate, alpha-ionone, beta-ionone, anisaldehyde, anisyl acetate, anisyl formate, benzaldehyde, benzothiazole, benzyl acetate, benzyl alcohol, benzyl benzoate, beta-ionone, butyl butyrate, butyl caproate, butylidene phthalide, carvone, camphene, caryophyllene, cineole, cinnamyl acetate, citral, citronellol, citronellal, citronellyl acetate, cyclohexyl acetate, cymene, damascone, decalactone, dihydrocoumarin, dimethyl anthranilate, dodecalactone, ethoxyethyl acetate, ethylbutyric acid, ethyl butyrate, ethyl caprate, ethyl caproate, ethyl crotonate, ethylfuraneol, ethylguaiacol, ethyl isobutyrate, ethyl isovalerate, ethyl lactate, ethyl methylbutyrate, ethyl propionate, eucalyptol, eugenol, ethyl heptylate, 4-(p-hydroxyphenyl)-2-butanone, gamma-decalactone, geraniol, geranyl acetate, grapefruit aldehyde, methyl dihydrojasmonate (e.g. Hedion®), heliotropin, 2-heptanone, 3-heptanone, 4-heptanone, trans-2-heptenal, cis-4-heptenal, trans-2-hexenal, cis-3-hexenol, trans-2-hexenic acid, trans-3-hexenic acid, cis-2-hexenyl acetate, cis-3-hexenyl acetate, cis-3-hexenyl caproate, trans-2-hexenyl caproate, cis-3-hexenyl formate, cis-2-hexyl acetate, cis-3-hexyl acetate, trans-2-hexyl acetate, cis-3-hexyl formate, para-hydroxybenzylacetone, isoamyl alcohol, isoamylisovalerate, isobutyl butyrate, isobutyraldehyde, isoeugenol methyl ether, isopropyl methylthiazole, lauric acid, laevulinic acid, linalool, linalool oxide, linalyl acetate, menthol, menthofuran, methyl anthranilate, methylbutanol, methylbutyric acid, 2-methylbutyl acetate, methyl caproate, methyl cinnamate, 5-methylfurfural, 3,2,2-methyl-cyclopentenolone, 6,5,2-methylheptenone, methyl dihydrojasmonate, methyl jasmonate, 2-methylmethylbutyrate, 2-methyl-2-pentenolic acid, methyl thiobutyrate, 3,1-methylthio-hexanol, 3-methylthiohexyl acetate, nerol, neryl acetate, trans,trans-2,4-nonadienal, 2,4-nonadienol, 2,6-nonadienol, nootkatone, delta-octalactone, gamma-octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl isovalerate, piperonal, propionaldehyde, propyl butyrate, pulegone, pulegol, sinensal, sulfurol, terpinene, terpineol, terpinolene, 8,3-thiomenthanone, 4,4,2-thiomethylpentanone, thymol, delta-undecalactone, gamma-undecalactone, valencene, valeric acid, vanillin, acetoin, ethylvanillin, ethylvanillin isobutyrate (=3-ethoxy-4-isobutyryloxybenzaldehyde), 2,5-dimethyl-4-hydroxy-3(2H)-furanone and derivatives thereof (here preferably homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (here preferably ethylmaltol), coumarin and coumarin derivatives, gamma-lactones (here preferably gamma-undecalactone, gamma-nonalactone, gamma-decalactone), delta-lactones (here preferably 4-methyldeltadecalactone, massoilactone, delta-decalactone, tuberolactone), methyl sorbate, divanillin, 4-hydroxy-2-(or 5)-ethyl-5-(or 2)-methyl-3(2H)furanone, 2-hydroxy-3-methyl-2-cyclopentenone, 3-hydroxy-4,5-dimethyl-2(5H)-furanone, isoamyl acetate, ethyl butyrate, n-butyl butyrate, isoamyl butyrate, ethyl 3-methylbutyrate, ethyl n-hexanoate, allyl n-hexanoate, n-butyl n-hexanoate, ethyl n-octanoate, ethyl-3-methyl-3-phenylglycidate, ethyl 2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio)furan, 2-methyl-3-furanthiol, bis(2-methyl-3-furyl)disulphide, furfuryl mercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnamaldehyde, cinnamyl alcohol, methyl salicylate, isopulegol and also (not explicitly stated here) stereoisomers, enantiomers, positional isomers, diastereomers, cis/trans isomers or epimers of these substances.

Chewing Gums

The preferred oral preparations may also be chewing gums. These products typically contain a water-insoluble component and a water-soluble component.

The water-insoluble base, also known as "gum base", usually comprises natural or synthetic elastomers, resins, fats and oils, plasticizers, fillers, dyes and also optionally waxes. The fraction of base of the total composition is usually 5 to 95% by weight, preferably 10 to 50% by weight and in particular 20 to 35% by weight. In a typical embodiment of the invention, the base is composed of 20 to 60% by weight synthetic elastomers, 0 to 30% by weight natural elastomers, 5 to 55% by weight plasticizers, 4 to 35% by weight fillers and in subsidiary amounts additives such as dyes, antioxidants and the like, with the proviso that they are water-soluble at most in small amounts.

Suitable synthetic elastomers are, for example, polyisobutylenes having average molecular weights (according to GPC) of 10,000 to 100,000, and preferably 50,000 to 80,000, isobutylene-isoprene-copolymers ("butyl elastomers"), styrene-butadiene-copolymers (styrene:butadiene ratio e.g. 1:3 to 3:1), polyvinylacetates having average molecular weights (according to GPC) of 2000 to 90,000, and preferably 10,000 to 65,000, polyisoprenes, polyethylene, vinyl acetate-vinyl laurate copolymers and mixtures thereof. Examples of suitable natural elastomers are rubbers, for instance smoked or liquid latex or Guayule and also natural rubbers such as jelutong, lechi caspi, perillo, sorva, massaranduba balata, massaranduba chocolate, nispero, rosindinba, chicle, gutta hang kang, and also mixtures thereof. The selection of synthetic and natural elastomers and mixing ratios thereof is governed substantially according to whether bubbles are to be generated ("bubble gums") or not with the chewing gums. Preferably, elastomer mixtures are used which contain jelutong, chicle, sorva and massaranduba.

In most cases, the elastomers prove in processing to be too hard or insufficiently manageable, and so it has proved advantageous to use conjointly specific plasticizers which of course must in particular also meet all the requirements to be permitted as food additives. In this respect, chiefly esters of resin acids come into consideration, for example esters of lower aliphatic alcohols or polyols with completely or partially hardened, monomeric or oligomeric resin acids. In particular for this purpose, the methyl, glycerol or pentaerythrityl esters and also mixtures thereof are used. Alternatively, terpene resins also come into consideration, and can be derived from alpha-pinene, beta-pinene, delta-limonene or mixtures thereof.

Suitable fillers or texturizing agents include magnesium or calcium carbonate, ground pumice stone, silicates, especially magnesium or aluminum silicates, clays, aluminas, talc, titanium dioxide, mono-, di- and tricalcium phosphate and also cellulose polymers.

Suitable emulsifiers are tallow, hardened tallow, hardened or partially hardened vegetable oils, cocoa butter, partial glycerides, lecithin, triacetin and saturated or unsaturated fatty acids having 6 to 22, and preferably 12 to 18, carbon atoms, and also mixtures thereof.

As dyes and whitening agents, for example the FD and C types, plant and fruit extracts and also titanium dioxide permitted for coloring foods come into consideration.

The base compositions can contain waxes or be wax-free; examples of wax-free compositions may be found, inter alia, in the patent document U.S. Pat. No. 5,286,500, the content of which is hereby explicitly incorporated by reference.

In addition to the water-insoluble gum base, chewing gum preparations regularly contain a water-soluble fraction which is formed, for example, by softeners, sweeteners, fillers, taste substances, taste intensifiers, emulsifiers, dyes, acidulants, antioxidants and the like, here with the proviso that the components have an at least adequate water solubility. Depending on the water solubility of the specific representatives, therefore, individual components can belong either to the water-insoluble phase or else the water-soluble phase. However, it is also possible to use combinations, for example of a water-soluble emulsifier and a water-insoluble emulsifier, in which case the individual representatives are then situated in different phases. Usually, the water-insoluble fraction makes up 5 to 95% by weight, and preferably 20 to 80% by weight, of the preparation.

Water-soluble softeners or plasticizing agents are added to the chewing gum compositions in order to improve the chewability and the chewing feel and are present in the mixtures typically in amounts of 0.5 to 15% by weight. Typical examples are glycerol, lecithin and also aqueous solutions of sorbitol, hardened starch hydrolysates or corn syrup.

As sweeteners, both sugar-containing and sugar-free compounds come into consideration and are used in amounts of 5 to 95% by weight, preferably 20 to 80% by weight, and in particular 30 to 60% by weight, based on the chewing gum composition. Typical saccharide sweeteners are sucrose, dextrose, maltose, dextrin, dried invert sugar, fructose, levulose, galactose, corn syrup, and also mixtures thereof. As sugar replacers, sorbitol, mannitol, xylitol, hardened starch hydrolysates, maltitol and mixtures thereof come into consideration. In addition, as additives, what are termed High Intensity Artificial Sweeteners (HIAS) also come into consideration, such as, for example, sucralose, aspartame, acesulfame salts, alitame, saccharin and saccharin salts, cyclamic acid and salts thereof, glycyrrhizins, dihydrochalcones, thaumatin, monellin and the like, alone or in blends. Also particularly effective are the hydrophobic HIAS which are subject-matter of international patent application WO 2002 091849 A1 (Wrigleys), and also stevia extracts and their active constituents, especially rebaudioside A. The amount in which the substances are used is dependent primarily on their performance capacity, and is situated typically in the range from 0.02 to 8% by weight.

In particular, for the production of low-calorie chewing gums, fillers such as, for example, polydextrose, raftilose, Rafitilin, fructooligosaccharides (NutraFlora), palatinose oligosaccharides, guar gum hydrolysates (Sun Fiber) and also dextrins are suitable.

The selection of further taste substances is virtually unlimited and is non-critical for the essence of the invention. Usually, the total fraction of all taste substances is 0.1 to 15% by weight, and preferably 0.2 to 5% by weight, based on the chewing gum composition. Suitable further taste substances are, for example, essential oils, synthetic flavorings and the like, such as, for instance, aniseed oil, star anise oil, caraway oil, eucalyptus oil, fennel oil, lemon oil, wintergreen oil, clove oil and the like, as are also used, for example, in oral and dental care compositions.

The chewing gums can in addition contain further auxiliaries and additives which are suitable, for example, for tooth care, especially for combating plaque and gingivitis, such as, e.g., chlorhexidine, CPC or triclosan. In addition, pH regulators (e.g. buffers or urea), substances active against caries (e.g. phosphates or fluorides), biogenic active ingredients (antibodies, enzymes, caffeine, plant extracts) may be present, provided that these substances are permitted for foods and do not interact with one another in an undesired manner.

Oral and Dental Care Compositions

Sweet-tasting products according to the invention that are consumable orally may also serve for oral and dental cleansing and care. Examples thereof are toothpastes, tooth gels, tooth powders, mouthwashes and the like. Toothpastes or tooth creams are generally taken to mean gel-type or pasty preparations of water, thickeners, humectants, abrasive or cleaning bodies, surfactants, sweeteners, aroma substances, deodorizing active ingredients and also active ingredients against oral and dental diseases. All customary cleaning bodies, such as, e.g., chalk, dicalcium phosphate, insoluble sodium metaphosphate, aluminum silicates, calcium pyrophosphate, finely divided synthetic resins, silicas, aluminum oxide and aluminum oxide trihydrate can be used in the toothpastes according to the invention.

Preferably suitable cleaning bodies for the toothpastes according to the invention are, especially, finely divided xerogel silicas, hydrogel silicas, precipitated silicas, aluminum oxide trihydrate and finely divided alpha-aluminum oxide or mixtures of these cleaning bodies in amounts of 15 to 40% by weight of the toothpaste. As humectants, principally low-molecular-weight polyethylene glycols, glycerol, sorbitol or mixtures of these products in amounts up to 50% by weight come into consideration. Among the known thickeners, the thickening, finely divided gel silicas and hydrocolloids, such as, e.g., carboxymethylcellulose, hydroxyethylcellulose, hydroxypropyl guar, hydroxyethyl starch, polyvinylpyrrolidone, high-molecular-weight polyethylene glycol, plant gums such as tragacanth, agar-agar, carrageen moss, gum arabic, xanthan gum and carboxyvinyl polymers (e.g. Carbopol® types) are suitable. In addition to the mixtures of menthofuran and menthol compounds, the oral and dental care compositions can in particular comprise surface-active substances, preferably anionic and nonionic high-foam surfactants, such as the aforementioned substances, but in particular alkylether sulfate salts, alkylpolyglucosides and mixtures thereof.

Further customary toothpaste additives are:
preservatives and antimicrobial substances such as, e.g. methyl, ethyl or propyl p-hydroxybenzoates, sodium sorbate, sodium benzoate, bromochlorophene, phenyl salicylic esters, thymol and the like;

antitartar active ingredients, e.g. organophosphates such as 1-hydroxyethane-1,1-diphosphonic acid, 1-phosphonpropane-1,2,3-tricarboxylic acid and others, which are known, e.g., from U.S. Pat. No. 3,488,419, DE 2224430 A1 and DE 2343196 A1;

other anticaries substances such as, e.g., sodium fluoride, sodium monofluorophosphate, tin fluoride;

sweetening agents, such as, e.g., saccharin sodium, sodium cyclamate, sucrose, lactose, maltose, fructose or aspartame, (L-aspartyl-L-phenylalanine methyl ester), stevia extracts or the sweetening components thereof, in particular rebaudiosides;

additional flavorings such as, e.g., eucalyptus oil, aniseed oil, fennel oil, caraway oil, methyl acetate, cinnamaldehyde, anethol, vanillin, thymol and also mixtures of these and other natural and synthetic flavorings;

pigments such as, e.g., titanium dioxide;

dyes;

buffer substances such as, e.g., primary, secondary or tertiary alkali metal phosphates or citric acid/sodium citrate;

Further customary toothpaste additives are wound-healing and antiinflammatory substances such as, e.g., allantoin, urea, azulene, chamomile active ingredients and acetylsalicylic acid derivatives.

One preferred embodiment of the oral preparations is toothpastes in the form of an aqueous, pasty dispersion, containing polishing agents, humectants, viscosity regulators and optionally further customary components, and also the mixture of menthofuran and menthol compounds in amounts of 0.5 to 2% by weight.

In mouthwashes, a combination with aqueous-alcoholic solutions of various concentration gradients of essential oils, emulsifiers, astringent and toning drug extracts, tartar-inhibiting, antibacterial additives and flavor correctors is easily possible. A further preferred embodiment of the invention is a mouthwash in the form of an aqueous or aqueous-alcoholic solution containing the mixture of menthofuran and menthol compounds in amounts of 0.5 to 2% by weight. In mouthwashes which are diluted before application, adequate effects can be achieved with higher concentrations corresponding to the intended dilution ratio.

To improve the flow behavior, in addition, hydrotropic agents, for example ethanol, isopropyl alcohol or polyols can be used; these substances correspond substantially to the carriers described at the outset. Polyols which come into consideration here preferably have 2 to 15 carbon atoms and at least two hydroxyl groups. The polyols can contain even further functional groups, in particular amino groups, and/or be modified by nitrogen. Typical examples are glycerol;

alkylene glycols, such as, for example, ethylene glycol, diethylene glycol, propylene glycol, butylene glycol, hexylene glycol and also polyethylene glycols having an average molecular weight from 100 to 1,000 daltons;

technical oligoglycerol mixtures having a degree of self-condensation of 1.5 to 10 such as technical diglycerol mixtures having a diglycerol content of 40 to 50% by weight;

methylol compounds such as, in particular, trimethylolethane, trimethylolpropane, trimethylolbutane, pentaerythritol and dipentaerythritol;

lower alkylglucosides, in particular those having 1 to 8 carbon atoms in the alkyl radical, such as, for example, methyl- and butyl-glucoside;

sugar alcohols having 5 to 12 carbon atoms, such as, for example, sorbitol or mannitol, sugars having 5 to 12 carbon atoms, such as, for example, glucose or sucrose;

amino sugars, such as, for example, glucamine;

dialcoholamines, such as diethanolamine or 2-amino-1,3-propanediol.

Suitable preservatives are, for example, phenoxyethanol, formaldehyde solution, parabens, pentanediol or sorbic acid, and also the silver complexes known under the name Surfacine® and the further classes of substances listed in annex 6, part A and B of the cosmetics regulation.

Perfume oils which may be mentioned are mixtures of natural and synthetic odor substances. Natural odorants are extracts of blossoms (lily, lavender, roses, jasmine, neroli, ylang-ylang), stalks and leaves (geranium, patchouli, petitgrain), fruits (aniseed, coriander, cumin, juniper), fruit skins (bergamot, lemon, oranges), roots (mace, angelica, celeriac, cardamom, costus, iris, calmus), woods (pine, sandal, guaiac, cedar, rosewood), herbs and grasses (tarragon, lemon grass, sage, thyme), needles and twigs (spruce, fir, pine, mountain pine), resins and balsams (galbanum, elemi, benzoin, myrrh, olibanum, opoponax). In addition, animal raw materials come into consideration, such as, for example, civet and castoreum. Typical synthetic odorant compounds are products of the type of esters, ethers, aldehydes, ketones, alcohols and hydrocarbons. Odorant compounds of the ester type are, e.g. benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexylpropionate, styrallyl propionate and benzyl salicylate. The ethers include, for example, benzyl ethyl ether, the aldehydes include, e.g. the linear alkanals having 8 to 18 carbon atoms, citral, citronellal, citronellyloxyacetaldehyde, cyclamen aldehyde, hydroxycitronellal, lilial and bourgeonal, the ketones include, e.g., the ionones, $\alpha$-isomethylionone and methyl cedryl ketone, the alcohols include anethole, citronellol, eugenol, isoeugenol, geraniol, linalool, phenylethyl alcohol and terpineol, the hydrocarbons include chiefly the terpenes and balsams. However, preference is given to using mixtures of various odorants which together generate a corresponding fragrance note. Also essential oils of lower volatility which are generally used as aroma components are suitable as perfume oils, e.g. salvia oil, chamomile oil, clove oil, melissa oil, mint oil, cinnamon leaf oil, linden blossom oil, juniper berry oil, vetiver oil, olibanum oil, galbanum oil, labolanum oil and lavender oil. Preferably, bergamot oil, dihydromyrcenol, lilial, lyral, citronellol, phenylethyl alcohol, $\alpha$-hexylcinnamaldehyde, geraniol, benzylacetone, cyclamen aldehyde, linalool, boisambrene forte, Ambroxan, indole, hedione, sandelice, lemon oil, mandarin oil, orange oil, allyl amyl glycolate, cyclovertal, lavender oil, *Salvia sclarea* oil, $\beta$-damascone, geranium bourbon oil, cyclohexyl salicylate, Vertofix Coeur, Iso E Super, Fixolide NP, evernyl, iraldein gamma, phenylacetic acid, geranyl acetate, benzyl acetate, rose oxide, romilllate, irotyl and floramate are used alone or in mixtures.

As flavorings, for example, peppermint oil, spearmint oil, aniseed oil, star anise oil, caraway oil, eucalyptus oil, fennel oil, lemon oil, wintergreen oil, clove oil, menthol and the like come into consideration.

INDUSTRIAL APPLICABILITY

The invention, further, also encompasses a method for reducing the oxidative degradation of monocyclic terpenes, which involves adding thereto an effective amount, as for example approximately 0.1 time to approximately 10 times, preferably approximately 0.5 time to approximately 5 times and more particularly approximately 1 time to approximately 3 times the amount, of propane-1,3-diol.

Furthermore, the invention also relates to the use of propane-1,3-diol for reducing the oxidative degradation of monocyclic terpenes, with the preferred amounts for use corresponding to those above.

pronounced caraway note, this is not only prevented by the addition of small amounts of propane-1,3-diol, but the citrus note is even enhanced.

Formulation Examples

TABLE 2a

Chewing gum compositions

| Composition | A | B | C | D | E | F | G | H |
|---|---|---|---|---|---|---|---|---|
| Polyisobutylene (MW 20.000) | 30.0 | 30.0 | 30.0 | 40.0 | 20.0 | 20.0 | 25.0 | 30.0 |
| Glucose | 51.0 | 51.0 | 51.0 | 42.5 | — | — | — | — |
| Corn syrup | 10.0 | 10.0 | 10.0 | 8.0 | — | — | — | — |
| Sorbitol | — | — | — | — | 51.0 | 51.0 | 47.5 | 44.5 |
| Mannitol | — | — | — | — | 5.0 | 5.0 | 4.3 | 3.6 |
| Glycerol | 1.8 | 1.8 | 1.8 | 1.8 | 8.0 | 8.0 | 8.0 | 7.0 |
| Lycasin:glycerol (1:1) | — | — | — | — | 8.2 | 8.2 | 8.0 | 7.0 |
| Lecithin | — | — | — | — | 0.2 | 0.2 | 0.2 | 0.2 |
| D-Limonene/propane-1,3-diol (1:10) | 1.0 | 1.0 | 1.0 | 1.0 | 1.0 | 1.0 | 1.0 | 1.0 |
| Water | to 100 | | | | | | | |

EXAMPLES

Examples 1 to 5, Comparative Example C1

Various substance mixtures based on monoterpenes were used for preparing soft drinks, and the products were stored for 48 h at 20° C. Thereafter, the taste properties were assessed by a panel consisting of 5 trained testers, using a scale from 1 (absent) to 10 (highly pronounced). The compositions and results are compiled in table 1 hereinbelow. The data are means of 5 serial measurements. Examples 1 to 5 are in accordance with the invention, example C1 serves for comparison. Example S corresponds to the standard, i.e. the assessment of the taste of the starting product immediately after its preparation.

TABLE 1

Taste properties of soft drink formulations

| Composition | S | C1 | 1 | 2 | 3 | 4 | 5 |
|---|---|---|---|---|---|---|---|
| Sucrose | 10 | 10 | 10 | 10 | 10 | 10 | 10 |
| Citric acid | 0.2 | 0.2 | 0.2 | 0.2 | 0.2 | 0.2 | 0.2 |
| D-Limonene | 0.01 | 0.01 | 0.01 | 0.01 | 0.01 | 0.01 | 0.01 |
| Rebaudioside A | — | — | — | — | — | 0.01 | 0.01 |
| Propane-1,3-diol | — | — | 0.1 | 0.2 | 0.3 | 0.1 | 0.3 |
| Water | | | to 100 | | | | |
| Assessment of the taste | | | | | | | |
| Citrus note | 6 | 4 | 8 | 9 | 9 | 9 | 9 |
| Herbaceous note | 0 | 4 | 3 | 3 | 3 | 2 | 1 |
| Caraway note | 0 | 4 | 3 | 3 | 2 | 2 | 1 |
| Bitterness | 4 | 5 | 3 | 3 | 2 | 1 | 1 |

The examples and comparative examples demonstrate that the object of the invention is achieved in its entirety: while the starting formulation loses much of its fruity note on storage while developing a herbaceous taste with a TABLE 2b Toothpaste composition

| Component | Commercial product | Amount [% by weight] |
|---|---|---|
| Precipitated silica | Sident ® 12 DS | 18.0 |
| Silica thickener | Aerosil ® 200 | 0.8 |
| Sorbitol | | 17.5 |
| Glycerol | | 17.5 |
| Carboxymethylcellulose | Relatin ® 100 SR | 0.9 |
| Sodium lauryl sulfate | Texapon ® K1296 | 2.0 |
| Sodium fluoride | | 0.22 |
| Saccharin-sodium | | 0.2 |
| D-Limonene/propane-1,3-diol (1:10) | | 1.0 |
| Water | | to 100 |

TABLE 2c

Mouthwash composition

| Component | Commercial product | Amount [% by weight] |
|---|---|---|
| Ethanol (96%) | | 10.0 |
| Sorbitan monolaurate + 20 EO | Tween ® 20 | 0.4 |
| D-Limonene/propane-1,3-diol (1:10) | | 0.3 |
| Sorbitol (70% strength aqueous solution) | | 8.0 |
| Methyl p-hydroxybenzoate | | 0.2 |
| Water | | to 100 |

TABLE 2d

Sugar-free candy

| Component | X | XI | XII |
|---|---|---|---|
| Isomalt | 94.0 | 94.0 | 94.0 |
| Xylitol | 2.40 | 2.40 | 2.40 |
| D-Limonene/propane-1,3-diol (1:10) | 0.10 | 0.15 | 0.20 |

TABLE 2d-continued

| | Sugar-free candy | | |
|---|---|---|---|
| Component | X | XI | XII |
| Citric acid | 0.050 | 0.050 | 0.050 |
| Cherry flavor | 0.25 | 0.25 | 0.25 |
| Water | | to 100 | |

What is claimed is:

1. A substance mixture comprising
   (a) limonene,
   (b) propane-1,3-diol, and
   (c) active substances selected from the group consisting of
      (c1) rebaudiosides or plant extracts comprising them,
      (c2) steviosides or plant extracts comprising them,
      (c3) monatin,
      (c4) naringin,
      (c5) chalcones and hydrochalcones,
      (c6) mogrosides or plant extracts comprising them,
      (c7) rubusosides or plant extracts comprising them, and
      (c8) glycyrrhizic acid or plant extracts comprising it;
   wherein the substance mixture comprises
   (a) 10 to 50% by weight of limonene,
   (b) 45 to 25% by weight of propane-1,3-diol, and
   (c) 45 to 25% by weight of active substances,
   provided the quantity adds up to 100% by weight.

2. The substance mixture as claimed in claim 1, comprising D-limonene as component (a).

3. The substance mixture as claimed in claim 1, comprising rebaudioside A as component (c).

4. The substance mixture as claimed in claim 1, having a water content of less than 2% by weight.

5. The substance mixture as claimed in claim 1, in the form of capsules.

* * * * *